United States Patent [19]

Miyazawa et al.

[11] Patent Number: 4,900,473
[45] Date of Patent: Feb. 13, 1990

[54] OPTICALLY ACTIVE ALKANOYLOXY 2,5-DIPHENYL PYRIMIDINE AND LIQUID CRYSTAL COMPOSITIONS

[75] Inventors: Kazutoshi Miyazawa; Hiromichi Ioue; Shinichi Saito; Kouji Ohno, all of Yokohama; Makoto Ushioda, Kawasaki, all of Japan

[73] Assignee: Chisso Corporation, Osaka, Japan

[21] Appl. No.: 260,520

[22] Filed: Oct. 20, 1988

[30] Foreign Application Priority Data

Oct. 20, 1987 [JP] Japan ................. 62-262820

[51] Int. Cl.$^4$ .............. G02F 1/13; C09K 19/34; C07D 239/02
[52] U.S. Cl. ............... 252/299.61; 252/299.01; 350/350 R; 350/350 S; 544/335
[58] Field of Search ............. 252/299.61, 299.01; 350/350 R, 350 S; 544/335

[56] References Cited

U.S. PATENT DOCUMENTS

| | | | |
|---|---|---|---|
| 4,725,688 | 2/1988 | Taguchi et al. | 252/299.61 |
| 4,744,918 | 5/1988 | Heppke et al. | 252/299.61 |
| 4,764,636 | 8/1988 | Sasaki et al. | 252/299.61 |
| 4,818,430 | 4/1989 | Saito et al. | 252/299.61 |
| 4,820,839 | 4/1989 | Krause et al. | 252/299.61 |
| 4,834,904 | 5/1989 | Krause et al. | 252/299.61 |

FOREIGN PATENT DOCUMENTS

| | | | |
|---|---|---|---|
| 225195 | 6/1987 | European Pat. Off. | 252/299.61 |
| 248335 | 12/1987 | European Pat. Off. | 252/299.61 |
| 267758 | 5/1988 | European Pat. Off. | 252/299.61 |
| 3515373 | 11/1986 | Fed. Rep. of Germany | 252/299.61 |
| 240385 | 10/1986 | German Democratic Rep. | 252/299.61 |
| 257638 | 6/1988 | German Democratic Rep. | 252/299.61 |
| 61-215374 | 9/1986 | Japan | 252/299.61 |
| 62-22889 | 1/1987 | Japan | 252/299.61 |
| 63-253075 | 10/1988 | Japan | 252/299.61 |
| 8606401 | 11/1986 | World Int. Prop. O. | 252/299.61 |
| 8705018 | 8/1987 | World Int. Prop. O. | 252/299.61 |

Primary Examiner—Teddy S. Gron
Attorney, Agent, or Firm—Wenderoth, Lind & Ponack

[57] ABSTRACT

The present invention provides new optically active 2,5-diphenyl pyrimidine derivatives, optically active liquid crystal compositions containing the derivatives and electro optical elements comprising the compositions.

The derivatives have the following general formula:

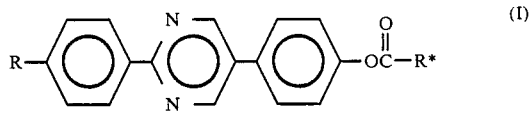

wherein R indicates an alkyl or alkoxy group having 2-20 carbon atoms and R* indicates an optically active alkyl group having 4-20 carbon atoms.

8 Claims, No Drawings

OPTICALLY ACTIVE ALKANOYLOXY 2,5-DIPHENYL PYRIMIDINE AND LIQUID CRYSTAL COMPOSITIONS

BACKGROUND OF THE INVENTION

The present invention relates to new optically active compounds and liquid crystal compositions containing the compounds, and more particularly, the present invention relates to optically active 2,5-diphenyl pyrimidine derivatives, optically active liquid crystal compositions containing the derivatives and electro optical elements using the compositions.

Liquid crystal display elements are widely used as various display elements, such as watches, electronic calculators, television sets, computer ends, etc., because these elements have excellent characteristics, such as operativity at low voltage, minimized consumption of electric power, obtainability of thin display elements and so on.

At present, display elements of a twisted nematic (TN) type are widely used as liquid crystal display elements. However, the response of the display element is slower than that of a display element of light emitting type such as an electroluminescence display, a plasma display, and the like. Although improvement of the response time of the liquid crystal display has been tried in many ways, it shows no sign of marked improvement.

However, a new display method using a ferroelectric liquid crystal that has been studied has hope for the improvement of the response time. (Clark et al., Appl. Phys. Lett., 36, 899(1980)). This display method utilizes a ferroelectric chiral smectic C phase (abbreviated as $S_c^*$ phase hereinafter) or other smectic phase such as a chiral smectic F, G, H or I phase, and the like. This method has a quick response time less than 1/100 to 1/1000 of that of the TN display method and a memory effect of bistability. It is expected to have wide application of a large sized television set of dynamic picture display, a high-speed light shutter, and the like.

However, in spite of these excellent characteristics, it is very difficult to find a compound having a preferable liquid crystal range for the chiral smectic liquid crystals different from the nematic liquid crystals which are used in the conventional TN type display method. Accordingly, compounds having a preferable liquid crystal range have been little known.

An object of the present invention is to provide optically active compounds having characteristics suited for the display method which is still being researched, especially having a preferable liquid crystal temperature range.

SUMMARY OF THE INVENTION

The present invention resides in a 2,5-diphenyl pyrimidine derivative represented by the following general formula:

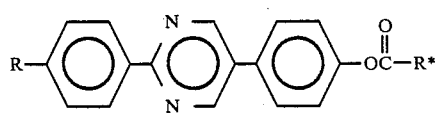

wherein R indicates an alkyl or alkoxy group having 2-20 carbon atoms, and R* indicates an optically active alkyl group having 4-20 carbon atoms. The present invention also resides in a liquid crystal composition containing at least one of the above compounds and an electro-optic element using the composition.

Hereupon, R* in formula (I) is preferably an optically active alkyl group having at least one branched methyl chain, such as

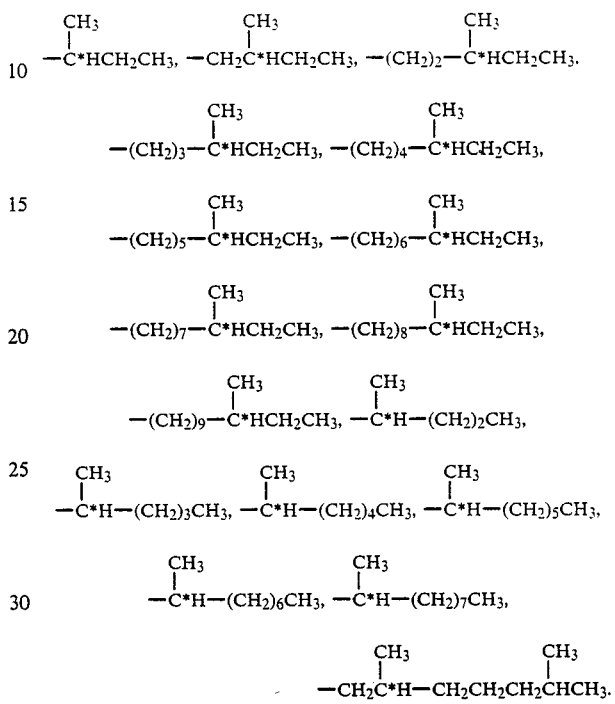

In known liquid crystal compounds having the chiral smectic C phase in a broad range of less than room temperature to 70°–80° C., there is no liquid crystal compound which can be used by itself. Accordingly, in order to reveal a sufficient chiral smectic phase range, several kinds of compounds which show the chiral smectic phase in relatively low temperature regions and compounds which show the chiral smectic phase in relatively high temperature regions have been mixed.

For the compounds which cover the high temperature regions, two conditions are required. The first condition is that maximum temperature of the chiral smectic phase is sufficiently raised and the second condition is that the melting point is not raised. As shown in the example 2 described hereinafter, the chiral smectic compounds of the present invention satisfy these conditions well.

The compounds of the present invention having asymmetric carbon atoms can induce twisted structure by adding them to nematic liquid crystals. As the nematic liquid crystals having the twisted structure, namely chiral nematic liquid crystals, do not produce so-called reverse twist domain of the TN type display element, the compounds of the present invention can be used as an inhibitor of the reverse twist domain.

The production method of the compounds of the present invention is described hereinafter.

An example of a method for preparing compound (I) of the present invention preferably includes the following process.

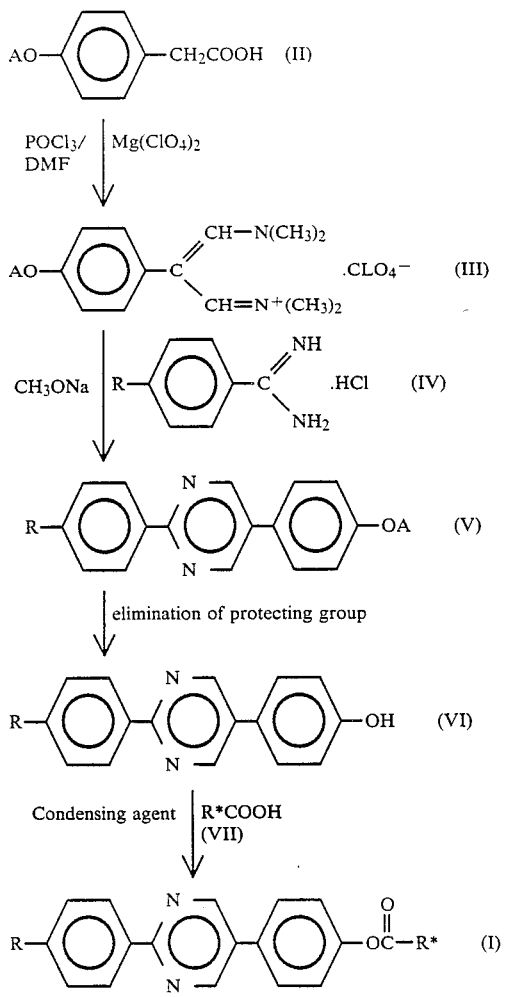

wherein R indicates an alkyl or an alkoxy group having 2–20 carbon atoms, R* indicates an optically active alkyl group having a 4–20 carbon atoms, and A indicates a protecting group such as methyl, benzyl and the like which can be eliminated.

Namely, compound (III) is obtained by reacting p-substituted phenylacetic acid (II) with phosphorus oxychloride, dimethylformamide and then a perchlorate such as magnesium perchlorate. Compound (V) is obtained by reacting compound (III) with p-alkyl benzamidine hydrochloride (IV) or p-alkoxy benzamidine hydrochloride under basic conditions. Compound (VI) is obtained by eliminating a protecting group of compound (V) by a certain method. Compounds (I) of the present invention are obtained by reacting the obtained compounds (V) and several kinds of carboxylic acids represented by the formula (VII).

The following compounds are representative compounds (I) of the present invention that are obtained by the above reaction and have preferable liquid crystal regions.

2-(4-butylphenyl)-5-[4-(4-methylhexanoyloxy)phenyl]-pyrimidine,
2-(4-butylphenyl)-5-[4-(5-methylheptanoyloxy)phenyl]-pyrimidine,
2-(4-butylphenyl)-5-[4-(6-methyloctanoyloxy)phenyl]-pyrimidine,
2-(4-butylphenyl)-5-[4-(7-methylnonanoyloxy)phenyl]-pyrimidine,
2-(4-butylphenyl)-5-[4-(8-methyldecanoyloxy)phenyl]-pyrimidine,
2-(4-pentylphenyl)-5-[4-(4-methylhexanoyloxy)phenyl]-pyrimidine,
2-(4-pentylphenyl)-5-[4-(5-methylheptanoyloxy)-phenyl]pyrimidine,
2-(4-pentylphenyl)-5-[4-(6-methyloctanoyloxy)phenyl]-pyrimidine,
2-(4-pentylphenyl)-5-[4-(7-methylnonanoyloxy)-phenyl]pyrimidine,
2-(4-pentylphenyl)-5-[4-(8-methyldecanoyloxy)phenyl]-pyrimidine,
2-(4-hexylphenyl)-5-[4-(4-methylhexanoyloxy)phenyl]-pyrimidine,
2-(4-hexylphenyl)-5-[4-(4-methylheptanoyloxy)phenyl]-pyrimidine,
2-(4-hexylphenyl)-5-[4-(4-methyloctanoyloxy)phenyl]-pyrimidine,
2-(4-hexylphenyl)-5-[4-(4-methylundecanoyloxy)-phenyl]pyrimidine,
2-(4-hexylphenyl)-5-[4-(5-methylheptanoyloxy)phenyl]-pyrimidine,
2-(4-hexylphenyl)-5-[4-(5-methyloctanoyloxy)phenyl]-pyrimidine,
2-(4-hexylphenyl)-5-[4-(5-methylundecanoyloxy)-phenyl]pyrimidine,
2-(4-hexylphenyl)-5-[4-(6-methyloctanoyloxy)phenyl]-pyrimidine,
2-(4-hexylphenyl)-5-[4-(6-methyldecanoyloxy)phenyl]-pyrimidine
2-(4-hexylphenyl)-5-[4-(6-methyldodecanoyloxy)-phenyl]pyrimidine,
2-(4-hexylphenyl)-5-[4-(7-methylnonanoyloxy)phenyl]-pyrimidine,
2-(4-hexylphenyl)-5-[4-(7-methyldecanoyloxy)phenyl]-pyrimidine,
2-(4-hexylphenyl)-5-[4-(8-methyldecanoyloxy)phenyl]-pyrimidine,
2-(4-hexylphenyl)-5-[4-(9-methylundecanoyloxy)-phenyl]pyrimidine,
2-(4-heptylphenyl)-5-[4-(2-methylbutyrloxy)phenyl]-pyrimidine,
2-(4-heptylphenyl)-5-[4-(2-methyloctanoyloxy)phenyl]-pyrimidine,
2-(4-heptylphenyl)-5-[4-(3-methylpentanoyloxy)-phenyl]pyrimidine,
2-(4-heptylphenyl)-5-[4-(4-methylhexanoyloxy)phenyl]-pyrimidine,
2-(4-heptylphenyl)-5-[4-(4-methylheptanoyloxy)-phenyl]pyrimidine,
2-(4-heptylphenyl)-5-[4-(4-methyloctanoyloxy)phenyl]-pyrimidine,
2-(4-heptylphenyl)-5-[4-(5-methylheptanoyloxy)-phenyl]pyrimidine,
2-(4-heptylphenyl)-5-[4-(5-methyldecanoyloxy)phenyl]-pyrimidine,
2-(4-heptylphenyl)-5-[4-(6-methyloctanoyloxy)phenyl]-pyrimidine,
2-(4-heptylphenyl)-5-[4-(6-methylnonanoyloxy)-phenyl]pyrimidine,
2-(4-heptylphenyl)-5-[4-(7-methylnonanoyloxy)-phenyl]pyrimidine,
2-(4-heptylphenyl)-5-[4-(7-methyldecanoyloxy)phenyl]-pyrimidine,
2-(4-heptylphenyl)-5-[4-(8-methyldecanoyloxy)phenyl]-pyrimidine, 2-(4-heptylphenyl)-5-[4-(8-methyldodecanoyloxy)-phenyl]pyrimidine,
2-(4-octylphenyl)-5-[4-(2-methylbutyryloxy)phenyl]-pyrimidine,
2-(4-octylphenyl)-5-[4-(2-methylpentanoyloxy)phenyl]-pyrimidine,
2-(4-octylphenyl)-5-[4-(2-methyloctanoyloxy)phenyl]-pyrimidine,
2-(4-octylphenyl)-5-[4-(3-methylpentanoyloxy)phenyl]-pyrimidine,
2-(4-octylphenyl)-5-[4-(3-methyloctanoyloxy)phenyl]-pyrimidine,
2-(4-octylphenyl)-5-[4-(4-methylhexanoyloxy)phenyl]-pyrimidine,
2-(4-octylphenyl)-5-[4-(4-methyloctanoyloxy)phenyl]-pyrimidine,
2-(4-octylphenyl)-5-[4-(4-methylundecanoyloxy)-phenyl]pyrimidine,
2-(4-octylphenyl)-5-[4-(5-methylheptanoyloxy)phenyl]-pyrimidine,
2-(4-octylphenyl)-5-[4-(5-methyldecanoyloxy)phenyl]-pyrimidine,
2-(4-octylphenyl)-5-[4-(6-methyloctanoyloxy)phenyl]-pyrimidine,
2-(4-octylphenyl)-5-[4-(6-methyltridecanoyloxy)-phenyl]pyrimidine,
2-(4-octylphenyl)-5-[4-(7-methylnonanoyloxy)phenyl]-pyrimidine,
2-(4-nonylphenyl)-5-[4-(2-methylbutyryloxy)phenyl]-pyrimidine,
2-(4-nonylphenyl)-5-[4-(2-methyloctanoyloxy)phenyl]-pyrimidine,
2-(4-nonylphenyl)-5-[4-(3-methylpentanoyloxy)-phenyl]pyrimidine,
2-(4-nonylphenyl)-5-[4-(3-methylhexanoyloxy)phenyl]-pyrimidine,
2-(4-nonylphenyl)-5-[4-(4-methylhexanoyloxy)phenyl]-pyrimidine,
2-(4-nonylphenyl)-5-[4-(4-methyldecanoyloxy)phenyl]-pyrimidine,
2-(4-nonylphenyl)-5-[4-(5-methylheptanoyloxy)-phenyl]pyrimidine,
2-(4-nonylphenyl)-5-[4-(5-methylnonanoyloxy)phenyl]-pyrimidine,
2-(4-nonylphenyl)-5-[4-(6-methyloctanoyloxy)phenyl]-pyrimidine,
2-(4-nonylphenyl)-5-[4-(6-methylnonanoyloxy)phenyl]-pyrimidine,
2-(4-nonylphenyl)-5-[4-(6-methyldecanoyloxy)phenyl]-pyrimidine,
2-(4-nonylphenyl)-5-[4-(6-methylundecanoyloxy)-phenyl]pyrimidine,
2-(4-nonylphenyl)-5-[4-(7-methylnonanoyloxy)phenyl]-pyrimidine,
2-(4-nonylphenyl)-5-[4-(7-methyldecanoyloxy)phenyl]-pyrimidine,
2-(4-nonylphenyl)-5-[4-(8-methyldecanoyloxy)phenyl]-pyrimidine,
2-(4-decylphenyl)-5-[4-(6-methyloctanoyloxy)phenyl]-pyrimidine,
2-(4-decylphenyl)-5-[4-(8-methyldecanoyloxy)phenyl]-pyrimidine,
2-(4-decylphenyl)-5-[4-(9-methylnonanoyloxy)phenyl]-pyrimidine,
2-(4-undecylphenyl)-5-[4-(8-methyldecanoyloxy)-phenyl]pyrimidine,
2-(4-undecylphenyl)-5-[4-(9-methylundecanoyloxy)-phenyl]pyrimidine,
2-(4-dodecylphenyl)-5-[4-(6-methyloctanoyloxy)-phenyl]pyrimidine,
2-(4-dodecylphenyl)-5-[4-(7-methylnonanoyloxy)-phenyl]pyrimidine,
2-(4-tridecylphenyl)5-[4-(7-methylnonanoyloxy)-phenyl]pyrimidine,
2-(4-tetradecylphenyl)-5-[4-(8-methyldecanoyloxy)-phenyl]pyrimidine,
2-(4-pentadecylphenyl)-5-[4-(6-methyloctanoyloxy)-phenyl]pyrimidine,
2-(4-butyloxyphenyl)-5-[4-(5-methylheptyloxy)phenyl]-pyrimidine,
2-(4-butyloxyphenyl)-5-[4-(6-methyloctyloxy)phenyl]-pyrimidine,
2-(4-butyloxyphenyl)-5-[4-(7-methylnonanoyloxy)-phenyl]pyrimidine,
2-(4-butyloxyphenyl)-5-[4-(8-methyldecanoyloxy)-phenyl]pyrimidine,
2-(4-pentyloxyphenyl)-5-[4-(4-methylhexanoyloxy)-phenyl]pyrimidine,
2-(4-pentyloxyphenyl)-5-[4-(5-methylheptanoyloxy)-phenyl]pyrimidine,
2-(4-pentyloxyphenyl)-5-[4-(6-methyloctanoyloxy)-phenyl]pyrimidine,
2-(4-pentyloxyphenyl)-5-[4-(7-methylnonanoyloxy)-phenyl]pyrimidine,
2-(4-pentyloxyphenyl)-5-[4-(8-methyldecanoyloxy)-phenyl]pyrimidine,
2-(4-hexyloxyphenyl)-5-[4-(4-methylhexanoyloxy)-phenyl]pyrimidine,
2-(4-hexyloxyphenyl)-5-[4-(4-methylheptanoyloxy)-phenyl]pyrimidine,
2-(4-hexyloxyphenyl)-5-[4-(4-methyloctanoyloxy)-phenyl]pyrimidine,
2-(4-hexyloxyphenyl)-5-[4-(5-methylheptanoyloxy)-phenyl]pyrimidine,
2-(4-hexyloxyphenyl)-5-[4-(5-methyloctanoyloxy)-phenyl]pyrimidine,
2-(4-hexyloxyphenyl)-5-[4-(5-methylundecanoyloxy)-phenyl]pyrimidine,
2-(4-hexyloxyphenyl)-5-[4-(6-methyloctanoyloxy)-phenyl]pyrimidine,
2-(4-hexyloxyphenyl)-5-[4-(6-methyldecanoyloxy)-phenyl]pyrimidine
2-(4-hexyloxyphenyl)-5-[4-(6-methyldodecanoyloxy)-phenyl]pyrimidine,
2-(4-hexyloxyphenyl)-5-[4-(7-methyldecanoyloxy)-phenyl]pyrimidine,
2-(4-hexyloxyphenyl)-5-[4-(8-methyldecanoyloxy)-phenyl]pyrimidine,
2-(4-hexyloxyphenyl)-5-[4-(9-methylundecanoyloxy)-phenyl]pyrimidine,
2-(4-heptyloxyphenyl)-5-[4-(2-methylbutyryloxy)-phenyl]pyrimidine,
2-(4-heptyloxyphenyl)-5-[4-(2-methyloctanoyloxy)-phenyl]pyrimidine,
2-(4-heptyloxyphenyl)-5-[4-(3-methylpentanoyloxy)-phenyl]pyrimidine,
2-(4-heptyloxyphenyl)-5-[4-(4-methylhexanoyloxy)-phenyl]pyrimidine,
2-(4-heptyloxyphenyl)-5-[4-(4-methylheptanoyloxy)-phenyl]pyrimidine,
2-(4-heptyloxyphenyl)-5-[4-(5-methylheptanoyloxy)-phenyl]pyrimidine,
2-(4-heptyloxyphenyl)-5-[4-(5-methyldecanoyloxy)-phenyl]pyrimidine,
2-(4-heptyloxyphenyl)-5-[4-(6-methyloctanoyloxy)-phenyl]pyrimidine, 2-(4-heptyloxyphenyl)-5-[4-(6-methylnonanoyloxy)-phenyl]pyrimidine,
2-(4-heptyloxyphenyl)-5-[4-(7-methylnonanoyloxy)-phenyl]pyrimidine,
2-(4-heptyloxyphenyl)-5-[4-(7-methyldecanoyloxy)-phenyl]pyrimidine,
2-(4-heptyloxyphenyl)-5-[4-(8-methyldecanoyloxy)-phenyl]pyrimidine,
2-(4-heptyloxyphenyl)-5-[4-(8-methyldodecanoyloxy)-phenyl]pyrimidine,
2-(4-octyloxyphenyl)-5-[4-(2-methylbutyryloxy)-phenyl]pyrimidine,
2-(4-octyloxyphenyl)-5-[4-(2-methylpentanoyloxy)-phenyl]pyrimidine,
2-(4-octyloxyphenyl)-5-[4-(2-methyloctanoyloxy)-phenyl]pyrimidine,
2-(4-octyloxyphenyl)-5-[4-(3-methylpentanoyloxy)-phenyl]pyrimidine,
2-(4-octyloxyphenyl)-5-[4-(3-methyloctanoyloxy)-phenyl]pyrimidine,
2-(4-octyloxyphenyl)-5-[4-(4-methylhexanoyloxy)-phenyl]pyrimidine,
2-(4-octyloxyphenyl)-5-[4-(4-methyloctanoyloxy)-phenyl]pyrimidine,
2-(4-octyloxyphenyl)-5-[4-(4-methylundecanoyloxy)-phenyl]pyrimidine,
2-(4-octyloxyphenyl)-5-[4-(5-methylheptanoyloxy)-phenyl]pyrimidine,
2-(4-octyloxyphenyl)-5-[4-(5-methyldecanoyloxy)-phenyl]pyrimidine,
2-(4-octyloxyphenyl)-5-[4-(6-methyloctanoyloxy)-phenyl]pyrimidine,
2-(4-octyloxyphenyl)-5-[4-(6-methyltridecanoyloxy)-phenyl]pyrimidine,
2-(4-octyloxyphenyl)-5-[4-(7-methylnonanoyloxy)-phenyl]pyrimidine,
2-(4-nonyloxyphenyl)-5-[4-(2-methylbutyryloxy)-phenyl]pyrimidine,
2-(4-nonyloxyphenyl)-5-[4-(2-methyloctanoyloxy)-phenyl]pyrimidine,
2-(4-nonyloxyphenyl)-5-[4-(3-methylpentanoyloxy)-phenyl]pyrimidine,
2-(4-nonyloxyphenyl)-5-[4-(3-methylhexanoyloxy)-phenyl]pyrimidine,
2-(4-nonyloxyphenyl)-5-[4-(4-methylhexanoyloxy)-phenyl]pyrimidine,
2-(4-nonyloxyphenyl)-5-[4-(4-methyldecanoyloxy)-phenyl]pyrimidine,
2-(4-nonyloxyphenyl)-5-[4-(5-methylheptanoyloxy)-phenyl]pyrimidine,
2-(4-nonyloxyphenyl)-5-[4-(5-methylnonanoyloxy)-phenyl]pyrimidine,
2-(4-nonyloxyphenyl)-5-[4-(6-methyloctanoyloxy)-phenyl]pyrimidine,
2-(4-nonyloxyphenyl)-5-[4-(6-methylnonanoyloxy)-phenyl]pyrimidine,
2-(4-nonyloxyphehyl)-5-[4-(6-methyldecanoyloxy)-phenyl]pyrimidine,
2-(4-nonyloxyphenyl)-5-[4-(7-methylnonanoyloxy)-phenyl]pyrimidine,
2-(4-nonyloxyphenyl)-5-[4-(7-methyldecanoyloxy)-phenyl]pyrimidine,
2-(4-nonyloxyphenyl)-5-[4-(8-methyldecanoyloxy)-phenyl]pyrimidine,
2-(4-decyloxyphenyl)-5-[4-(6-methyloctanoyloxy)-phenyl]pyrimidine,
2-(4-decyloxyphenyl)-5-[4-(8-methyldecanoyloxy)-phenyl]pyrimidine,
2-(4-decyloxyphenyl)-5-[4-(9-methylnonanoyloxy)-phenyl]pyrimidine,
2-(4-undecyloxyphenyl)-5-[4-(8-methyldecanoyloxy)-phenyl]pyrimidine,
2-(4-undecyloxyphenyl)-5-[4-(9-methylundecanoyloxy)phenyl]pyrimidine,
2-(4-dodecyloxyphenyl)-5-[4-(6-methyloctanoyloxy)-phenyl]pyrimidine,
2-(4-tridecyloxyphenyl)5-[4-(7-methylnonanoyloxy)-phenyl]pyrimidine,
2-(4-tetradecyloxyphenyl)-5-[4-(8-methyldecanoyloxy)-phenyl]pyrimidine,
2-(4-pentadecyloxyphenyl)-5-[4-(6-methyloctanoyloxy)phenyl]pyrimidine.

The merits of the present invention are as follows. According to the present invention, any of the compounds can be used as components of ferroelectric liquid crystals. These compounds having substantially high values of spontaneous polarization are applicable to liquid crystal materials, especially liquid crystal materials which enable electro optical display showing quick response.

Furthermore, when the compounds of the present invention are used as components of liquid crystal compositions, the compounds are very useful as components of ferroelectric liquid crystal materials showing preferable temperature regions of ferroelectric liquid crystal. Chiral nematic liquid crystal compositions obtained by adding the compounds of the present invention to nematic liquid crystal compositions are also useful as inhibitors of reverse twist domain.

DESCRIPTION OF PREFERRED EMBODIMENTS

The following examples illustrate the optically active compounds of the present invention more specifically.

EXAMPLE 1

Production of S-2-(4-nonylphenyl)-5-[4-(8-methyldecanoyloxy)phenyl]pyrimidine: (In the formula (I), R is $C_9H_{19}$-, R* is

To 366 g of dimethylformamide, 460 g of phosphorus oxychloride was added dropwise at 0° C., and then 156 g of p-methoxyphenylacetic acid was added little by little to the mixture at −10°. The mixture was stirred at 20° C. for one hour, at 60° C. for two hours and at 80° C. for five hours. Dimethylformamide was distilled away under vacuum, a solution saturated with magnesium perchlorate was added to the residue at −10° C. The obtained crystals were separated by filtration and washed with ether. A salt 191.2 g was obtained and its melting point was 133.3°–134.4° C.

A mixture of 60 g of the salt, 48 g of p-nonyl benzamidine hydrochloride, 13.6 g of sodium methoxide and 600 ml of ethanol was refluxed for eight hours. Toluene was added to the mixture. The mixture was washed with alkali solution and then with water. The solvent was distilled away. Recrystallization of the residue from a mixed solvent of ethanol and ethyl acetate gave 60 g of 2-(4-nonylphenyl)-5-(4-methoxyphenyl)pyrimidine. This compound showed liquid crystal property and its phase transition temperatures were as follows.

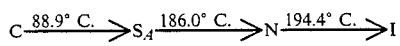

A mixture of 30 g of the above 2-(4-nonylphenyl)-5-(4-methoxyphenyl)pyrimidine, 120 g of 48% hydrobromic acid and 500 ml of acetic acid was refluxed for 40 hours. After acetic acid was distilled away, one liter of water was added to the residue. The obtained crystals were filtered and recrystallized from a solvent of n-heptane-ethyl acetate. 16.3 g of 2-(4-nonylphenyl)-5-(4-hydroxyphenyl)pyrimidine was obtained. This compound showed liquid crystal property and its phase transition temperatures were as follows.

A mixture of 5 g of the above 2-(4-nonylphenyl)-5-(4-hydroxyphenyl)pyrimidine, 3.8 g of S-8-methyldecanoic acid, 4.8 g of N,N'-dicyclohexylcarbodiimide, 0.35 g of 4-N,N-dimethylaminopyridine and 75 ml of dichloromethane was stirred at room temperature for two hours. The obtained crystals were filtered off, and the filtrate was washed with an alkali solution, and then with water. After the solvent was distilled away, the residue was recrystallized from a mixed solvent of ethanol-ethyl acetate, and 3 g of colorless needle-shaped crystals were obtained. By elemental analysis, NMR-spectrum and IR-spectrum, the obtained compound was S-2-(4-nonylphenyl)-5-[4-(8-methyldecanoyloxy)phenyl]pyrimidine.

This compound showed liquid crystal property and its phase transition temperatures were as follows.

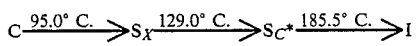

Further, the $S_X$ phase showed an unidentified smectic phase.

EXAMPLE 2 (Use Example 1)

Firstly, a composition comprising of the following liquid crystal compounds was prepared.

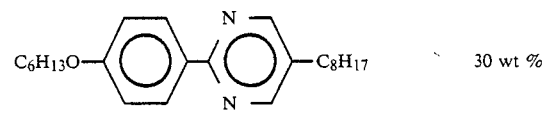

30 wt %

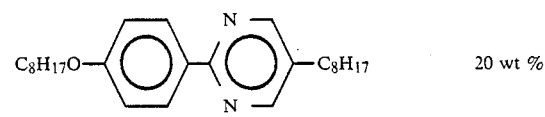

20 wt %

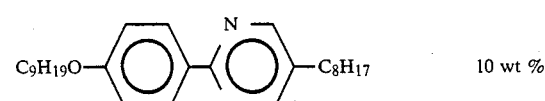

10 wt %

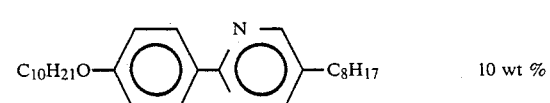

10 wt %

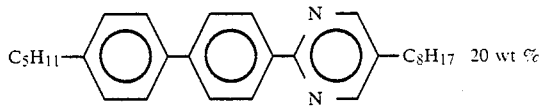

20 wt %

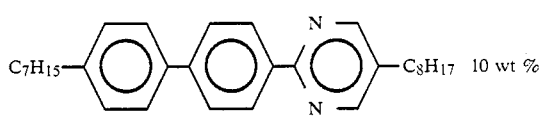

10 wt %

The phase transition temperatures of the above composition were as follows:

By adding 20% by weight of the compound of Example 1, namely S-2-(4-nonylphenyl)-5-[4-(8-methyldecanoyloxy)phenyl]pyrimidine to 80% by weight of the above composition, a chiral smectic composition was prepared.

When the composition was observed with a polarization microscope, it showed the following phase transition temperatures.

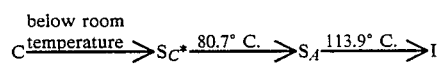

By adding the compounds (I) of the present invention, the upper limit of the $S_C^*$ phase increased above 15° C., and it was confirmed that the compounds (I) of the present invention were very useful ferroelectric liquid crystal compounds.

EXAMPLE 3 (Use Example 2)

A nematic liquid crystal composition containing the following compounds:

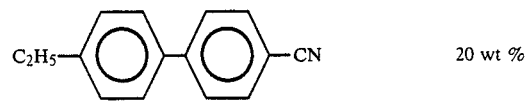

20 wt %

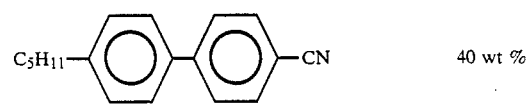

40 wt %

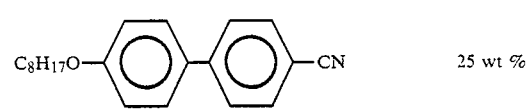

25 wt %

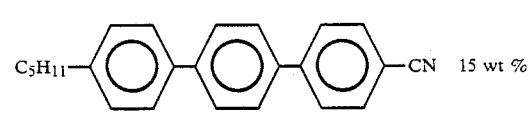

15 wt % was injected into a cell of 10 μm thickness having transparent electrodes, the surface of which was treated by the application of polyvinylalcohol as an aligning agent and by the rubbing for parallel aligning treatment. The resulting TN type cell was observed with a polarization 5 microscope, and it was found that reverse twist domain was produced.

To the above nematic liquid crystal composition, 1 percent by weight of the compound of Example 1, namely S-2-(4-nonylphenyl)-5-[4-(8-methyldecanoyloxy)phenyl]pyrimidine was added. The TN cell obtained by the same method as described above was observed with the polarization microscope. The reverse twist domain was dissolved and a homogeneous mematic phase was observed.

What we claim is:

1. A 2,5-diphenyl pyrimidine derivative represented by the formula:

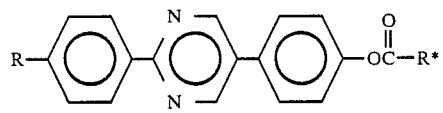

wherein R is alkyl of 5–15 carbon atoms, and R* is optically active alkyl of 5–11 carbon atoms.

2. A 2,5-diphenyl pyrimidine derivative as claimed in claim 1, wherein R* is

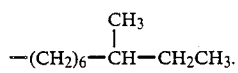

3. A 2,5-diphenyl pyrimidine derivative as claimed in claim 1, namely S-2-(4-nonylphenyl)-5-[4-(8-methyldecanoyloxy)phenyl]pyrimidine.

4. A liquid crystal composition comprising at least two components, at least one of which is a 2,5-diphenyl pyrimidine derivative as set forth in claim 1.

5. A liquid crystal composition as claimed in claim 4, exhibiting a chiral smectic phase.

6. A liquid crystal composition as claimed in claim 5, wherein the composition comprises, in addition to the 2,5-diphenyl pyrimidine derivative, the following liquid crystal compounds:

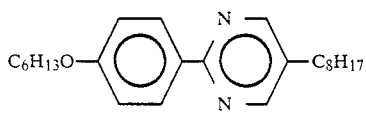

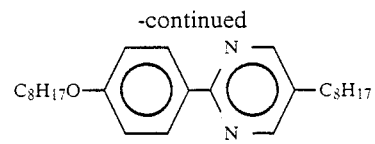

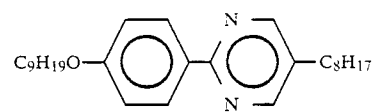

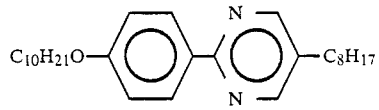

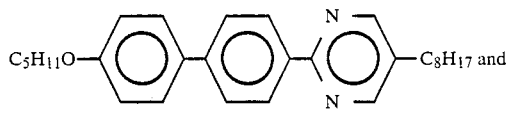

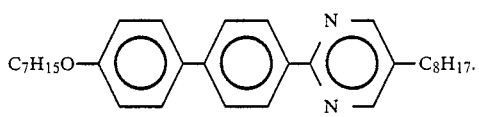

7. A liquid crystal composition as claimed in claim 4, exhibiting a chiral nematic phase.

8. A liquid crystal composition as claimed in claim 7, wherein the composition comprises, in addition to the 2,5-diphenyl pyrimidine derivative, the following compounds:

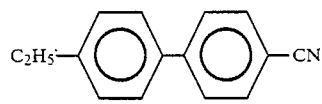

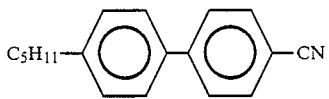

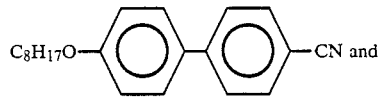

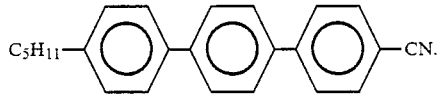

* * * * *